US011213461B2

(12) United States Patent
Dolan et al.

(10) Patent No.: US 11,213,461 B2
(45) Date of Patent: Jan. 4, 2022

(54) ENTERAL FEEDING TUBE HOUSING AND FIXATION DEVICES

(71) Applicant: Oregon Health & Science University, Portland, OR (US)

(72) Inventors: James P. Dolan, Portland, OR (US); Younes Jahangiri Noudeh, Portland, OR (US); Niloy Ghosh, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 147 days.

(21) Appl. No.: 16/335,167

(22) PCT Filed: Oct. 3, 2017

(86) PCT No.: PCT/US2017/055006
§ 371 (c)(1),
(2) Date: Mar. 20, 2019

(87) PCT Pub. No.: WO2018/067619
PCT Pub. Date: Apr. 12, 2018

(65) Prior Publication Data
US 2019/0274928 A1    Sep. 12, 2019

Related U.S. Application Data

(60) Provisional application No. 62/403,326, filed on Oct. 3, 2016, provisional application No. 62/545,339, filed on Aug. 14, 2017.

(51) Int. Cl.
*A61J 15/00* (2006.01)
*A61M 25/02* (2006.01)

(52) U.S. Cl.
CPC ........... *A61J 15/0061* (2013.01); *A61J 15/00* (2013.01); *A61J 15/0015* (2013.01);
(Continued)

(58) Field of Classification Search
CPC .... A61J 15/0061; A61J 15/00; A61J 15/0034; A61J 15/0015; A61J 15/0069; A61M 2025/0286
See application file for complete search history.

(56) References Cited

U.S. PATENT DOCUMENTS 5,916,200 A * 6/1999 Eppley ................. A61M 25/02
604/178
6,765,122 B1   7/2004 Stout
(Continued)

FOREIGN PATENT DOCUMENTS

EP   0807450 A1 * 11/1997 ............ A61M 25/02
EP   0807450 A1   11/1997

*Primary Examiner* — Theodore J Stigell
*Assistant Examiner* — Rachel T. Smith
(74) *Attorney, Agent, or Firm* — Schwabe, Williamson & Wyatt, P.C.

(57) ABSTRACT

Enteric feeding tube housings configured to secure a feeding tube to the body are disclosed. The housing includes a disc having a hole configured to accommodate the feeding tube and two or more holes configured to accommodate fasteners. Also disclosed are enteric feeding tube housings that include a disc having a hole configured to accommodate the feeding tube and two or more holes configured to accommodate fasteners, and a plurality of fasteners. Also disclosed are surgical kits that include a housing, a plurality of fasteners, and a plurality of locking devices configured to adjustably secure the fasteners in the fastener receiving holes, and method of using the disclosed devices.

14 Claims, 10 Drawing Sheets

(52) U.S. Cl.
CPC ....... *A61J 15/0034* (2013.01); *A61J 15/0069* (2013.01); *A61M 2025/0286* (2013.01)

(56) References Cited

U.S. PATENT DOCUMENTS

| | | |
|---|---|---|
| 8,323,316 B2 | 12/2012 | Maiorino et al. |
| 8,814,902 B2 | 8/2014 | Bonutti |
| 2008/0319397 A1 | 12/2008 | Macaluso |
| 2015/0224285 A1* | 8/2015 | Howell ................. A61M 25/02 604/180 |

* cited by examiner

ENTERAL FEEDING TUBE HOUSING AND FIXATION DEVICES

CROSS REFERENCE TO RELATED APPLICATIONS

The present application is a national phase entry under 35 U.S.C. § 371 of International Application No. PCT/US2017/055006, filed Oct. 3, 2017, which was published in English and designated, among the various States, the United States of America, which claims priority to U.S. Provisional Application No. 62/403,326, which was filed on Oct. 3, 2016, titled "FEEDING TUBE HOUSING," and to U.S. Provisional Application No. 62/545,339, which was filed on Aug. 14, 2017, titled "ENTERAL FEEDING TUBE HOUSING AND FIXATION DEVICES," both of which are hereby incorporated by reference in their entirety.

ACKNOWLEDGEMENT OF GOVERNMENT SUPPORT

This invention was made with government support under TR000128 awarded by the National Institutes of Health. The government has certain rights in the invention.

TECHNICAL FIELD

Embodiments relate to devices used in the securing of enteral feeding tubes, and, more specifically, to devices used external to the body to secure enteral feeding tubes.

BACKGROUND

Figure 1:
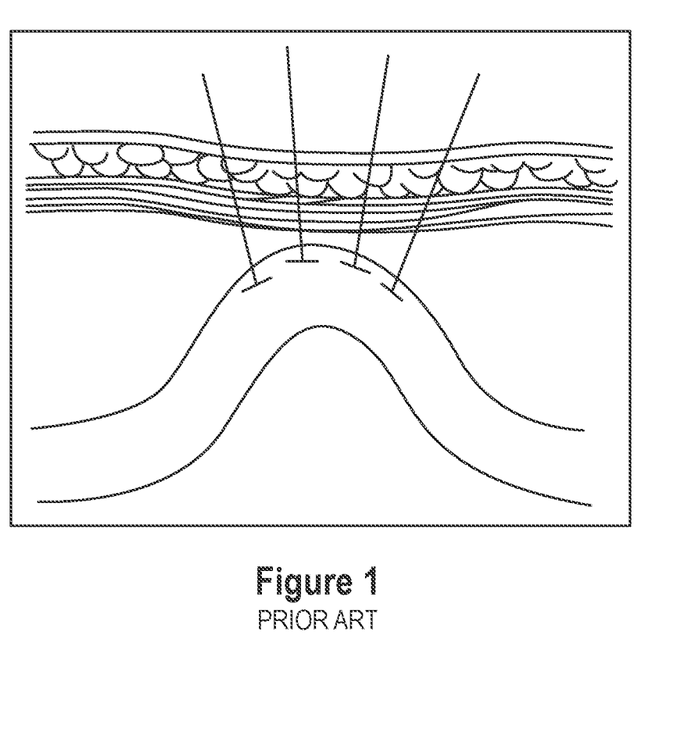
FIG. 1 is an illustration of a prior art system with locking skin anchors that secure the bowel to the abdominal wall and allow access to the intestines via a flexible plastic feeding tube.

Due to the dramatic increase of upper gastrointestinal malignancies worldwide, as well as surgical and medical problems in patients without cancer, there is an increased need for safe devices that provide access to the gastrointestinal tract. These devices allow patients who cannot accept oral intake to receive hydration, nutrition, and medication. Conventional surgical kits that are used to accomplish this access typically use a T-fastener system that secures a loop of bowel to the inside of the abdominal wall in four places. This system allows access to the bowel lumen for a flexible plastic feeding tube that is passed through the abdominal wall. An example of such a system is depicted in FIG. 1. Such systems are prone to breakage, time-consuming to place, and uncomfortable for the patient, as they cannot be adjusted once they have been placed.

In the past, additional commercially available kits were able to provide reliable, but uncomfortable enteral access. However, such kits have been removed from the market and are no longer available. This has resulted in surgeons using off-label devices or "patchwork" kits constructed from multiple sources. Not only is this approach dangerous for patients, but it also increases healthcare costs significantly. Serious complications, adverse medical outcomes, and increased hospital and healthcare costs have resulted from the failure of these alternate devices.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide systems and devices for securing an enteral feeding tube, such as a jejunal feeding tube, to the body of a patient for access to the intestines. In various embodiments, such systems and devices may include enteric feeding tube housings, improved fasteners, and fastener fixation devices. The disclosed systems and devices provide improved safety, ease of use, and reduced cost compared to conventional systems.

Many medical and surgical problems result in the inability of a patient to swallow and/or activate upper gastrointestinal tract mechanisms necessary for oral feeding and/or hydration. Additionally, there has been an increase in the incidence of upper gastrointestinal cancers worldwide, particularly esophageal and gastric cancers, that may lead to oral feeding problems. For example, in the United States, the incidence of esophageal adenocarcinoma has increased by over 1600% during the second half of the 20th century. These malignancies may cause obstruction, and patients may be unable to swallow food, water, or medications. Consequently, there is a growing need for devices to provide enteral nutrition at a point beyond the stomach.

Enteral feeding tubes typically are placed in the jejunum, which is the upper portion of the small bowel. Safe jejunostomy kits are no longer commercially available, and alternative devices been shown to have significant shortcomings. Various problems have been identified with these "makeshift" devices, especially in obese patients.

Thus, there is an increasing need for enteral feeding access systems in hospital populations, and enteric access generally is accomplished using a laparoscopic surgical approach. However, enteral tube placement with laparoscopic assistance is a time-consuming and awkward procedure requiring advanced laparoscopic skills, and adding significant time and cost to surgery. The typical approach incorporates intraabdominal (e.g., intracorporeal) suturing to fix the jejunum against the inside of the abdominal wall and allow secure placement of the feeding tube (e.g., the jejunostomy tube). An alternate technique is to use a specific kind of fastener (called a T-fastener) to pull and fix the bowel to the abdominal wall in one or more places and provide a foundation through which a jejunostomy tube may be passed into the jejunum.

A typical, commercially-available T-fastener device comprises an 8-inch long nylon thread attached vertically to a small ⅜-inch long metal piece at its end, forming a T shape. The device may be fixed to the abdominal skin surface through a mechanical button or soft pledget on the nylon thread. Originally, this fastener was designed to be used as the only fixator of the bowel without needing to also use intracorporeal sutures. In this configuration, fasteners are deployed to fix the bowel segment in a diamond or square formation around the percutaneously placed jejunostomy tube. FIG. 1 is an illustration of an example of a fastener system with locking skin anchors that secures the bowel to the abdominal wall and allows access to the intestines via a flexible plastic feeding tube.

Such fasteners may break and may then require surgical intervention to salvage the jejunostomy and save the patient from sepsis. Additionally, fixation devices, such as the one depicted in FIG. 1, may cause pain and local tissue compression that may promote skin infections and abscesses at the jejunostomy site. These complications may lead to poor patient outcomes and increased healthcare costs.

To prevent such device failings, alternate methods of jejunostomy placement have been developed, but such procedures may take over 30 minutes of expensive operating room time to install, as compared to a 15 minute procedure using current fastener systems. Thus, the presently-available jejunostomy systems and methods may result in patient discomfort, poor clinical outcomes, increased operating room utilization, and/or complications that increase the length of inpatient treatment.

Disclosed in various embodiments herein are feeding tube systems and devices, such as enteric feeding tube housings, improved fasteners, such as T-fasteners, and fastener fixation devices, that provide easier and more efficient placement of jejunal feeding tubes while also providing less pain and better clinical outcomes. Additionally, the disclosed systems and devices may save approximately 20 minutes of operating room time per procedure, compared to existing systems and methods. In various embodiments, this decrease in surgery time may also reduce anesthesia time and overall cost. Additionally, the systems disclosed herein provide a clean environment around the enteric access site and minimize patient pain and jejunal site leakage.

Disclosed herein are housings and fixation devices for providing access to the gastrointestinal tract and securing an enteral feeding tube to a subject's abdomen. In various embodiments, the feeding tube housing may include a disc, such as a substantially circular disc, with a first hole passing therethrough for accommodating a feeding tube. In various embodiments, this hole may be located in about the center of the disc, and the disc also may include a plurality of additional holes (e.g., second, third, fourth, fifth holes, etc.) that are referred to herein as fastener holes and that accommodate a corresponding plurality of fasteners, such as sutures and T-fasteners. Such an arrangement provides load distribution within the construct, thus addressing problems associated with individualized fixation devices.

While referred to as a disc, which may suggest a circular or substantially circular shape, the feeding tube housing may be any of a variety of shapes including oval, square, rectangular, etc. In some embodiments, the disc also may include a perforation, such as a substantially circular perforation, disposed about the first hole. In various embodiments, the perforation may divide the disc into two separate sections: a first section that includes the first hole, and a second section that includes the plurality of fastener receiving holes. In various embodiments, all of the holes may be substantially circular, although differently shaped holes may also be used such as oval, square, rectangular, etc.

Although T-fasteners are discussed throughout the disclosure, it should be understand that other fasteners (such as sutures and fasteners having one or more anchoring features that are not T-shaped) may be used provided they can be anchored at one end in the patient's tissue and at the other end coupled to the feeding tube housing.

In various embodiments, the housing may be constructed of any material, including plastic. In some embodiments, the housing also may include a silicone layer or pad coupled to the ventral (body-facing) side of the disc. In some embodiments, the silicone layer or pad may include an antibacterial composition, such as a composition that includes a silver compound.

Also disclosed in various embodiments are enteric feeding tube housing devices that include a disc having a first hole for accommodating a feeding tube, a plurality of fastener receiving holes disposed about the first hole and, a corresponding plurality of fasteners. In some embodiments, the fasteners are T-fasteners, and in particular embodiments each of the plurality of fasteners includes a graphene monofilament. Some embodiments of the device include a silicone pad coupled to a body-facing side of the disc, and the silicone pad may include an antibacterial composition.

Also disclosed herein are surgical kits that include a disc having a first hole for accommodating a feeding tube and a plurality of fastener receiving holes disposed about the first hole, a corresponding plurality of fasteners, and a corresponding plurality of fixation devices, each sized and shaped to fit within one of the fastener receiving holes. Each of the plurality of fixation devices may include a base member that has a bottom portion sized and shaped to fit within one of the fastener receiving holes, an aperture for receiving one of the plurality of the fasteners, and a sidewall extending from the bottom portion. In some embodiments, the sidewall may include one or more features for receiving and securing a locking component, such as a plurality of angled slots disposed on an inward-facing surface of the sidewall.

In some embodiments, the fixation device also may include a locking component having a disc-shaped body that includes a plurality of protruding tabs sized to slide within the plurality of angled slots in the base member. Optionally, the surgical kit also may include a pressure plate sized and shaped to fit within the sidewall of the base member and having an aperture sized and shaped for receiving one of the plurality of fasteners.

In use, the end of each protruding tab is configured to be journaled in a corresponding angled slot in the base member, and the plurality of angled slots define a range of movement of the protruding tabs as they slide within each slot when the locking component is rotated about a central axis. In various embodiments, the locking component may include a handle for rotating the locking component within the base member, and rotation of the locking component may reversibly lock a fastener disposed in the fixation device into a desired position.

Further embodiments include methods of securing a feeding tube that include surgically securing a portion of an intestine adjacent to an abdominal wall with a plurality of fasteners, and externalizing a portion of each of the plurality of fasteners by passing it through the abdominal wall. The fasteners may then be coupled to an enteric feeding tube housing device that is retained against the subject's skin. The feeding tube housing device may include a disc that includes first hole for accommodating a feeding tube and a plurality of fastener receiving holes disposed about the first hole. Once the enteric feeding tube housing has been placed, a feeding tube may be advanced through the first hole, through the abdominal wall, and into the portion of the intestine. In some embodiments, the fasteners may be T fasteners, and the method may also include reversibly locking each of the fasteners to the enteric feeding tube housing using a fixation device.

Figure 2:
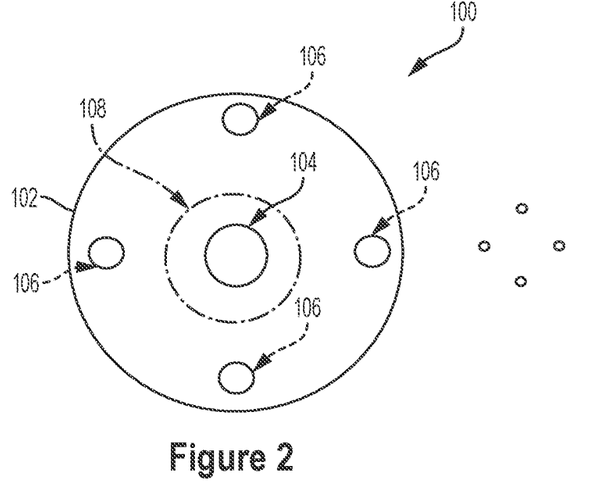
FIG. 2 is a top view of an example of a feeding tube housing as disclosed herein, in accordance with various embodiments.
Figure 3:
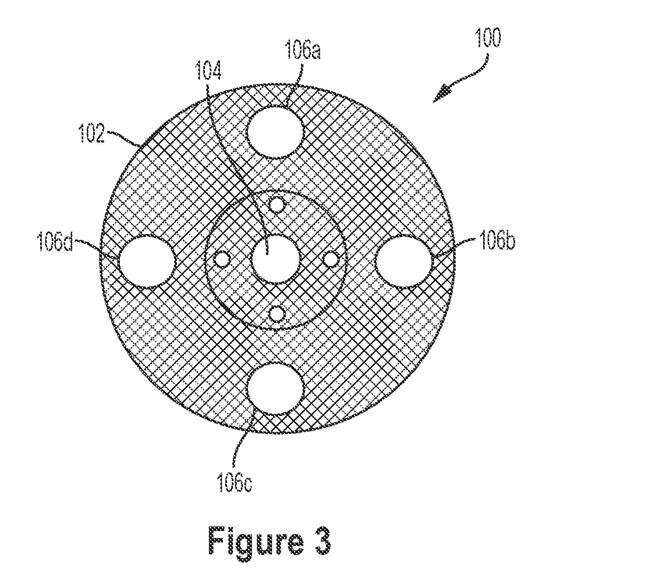
FIG. 3 is a top view of the feeding tube housing of FIG. 2, showing that lines passing through the first hole and pairs of opposing fastener receiving holes holes are substantially perpendicular, in accordance with various embodiments.

Referring now to the figures, in various embodiments, the systems and devices disclosed herein may include an enteric feeding tube housing that includes a disc. FIG. 2 is a top view of one example of a feeding tube housing 100, and includes a substantially circular disc 102 that includes a plurality of holes 104, 106; FIG. 3 is a top view of the feeding tube housing 100 of FIG. 2, showing that lines passing through the first hole 104 (which receives the feeding tube) and opposing pairs of T-fastener holes 106a, 106b, 106c, 106d are substantially perpendicular; and FIG. 4 is a perspective view of the feeding tube housing 100 of FIG. 2, all in accordance with various embodiments.

Figure 4:
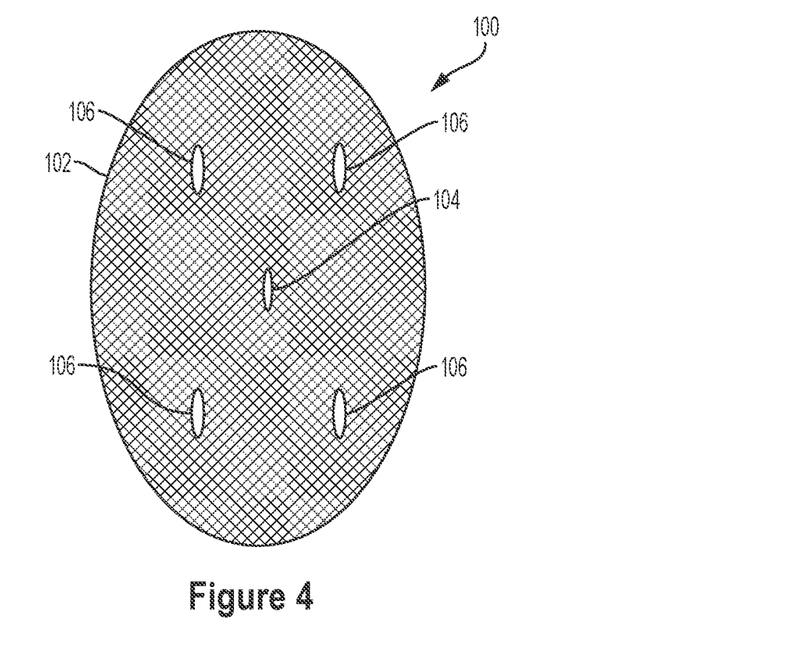
FIG. 4 is a perspective view of the feeding tube housing of FIG. 2, in accordance with various embodiments.

With reference to FIGS. 2-4, in various embodiments, the feeding tube housing 100 may have a first hole 104 that is sized and shaped to accommodate a feeding tube, such as a 10-20 French feeding tube. In various embodiments, the first hole 104 may be located in about the center of the disc 102, and the feeding tube housing 100 also may include a plurality of fastener receiving holes 106 that are positioned to receive a corresponding plurality of fasteners. In some embodiments, the feeding tube housing 100 may include two, three, four, five, or even more fastener receiving holes 106. Additionally, some embodiments may include a perforation 108 disposed around the first hole 102, where the perforation 108 divides the disc into a first section and a second section. In the illustrated embodiment, the first section includes the first hole 104 and the second section includes the plurality of fastener receiving holes 106. In some embodiments, perforation 108 may allow for securing or fixing the first section in place prior to or after the removal of the second section at the perforation line.

Figure 5:
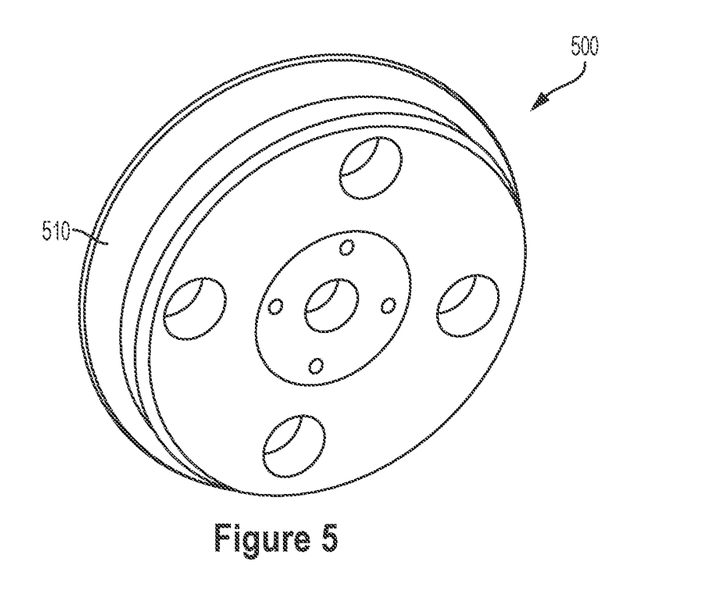
FIG. 5 is a 3-D rendering of a second example of a feeding tube housing that includes a silicone pad, in accordance with various embodiments.
Figure 6A:
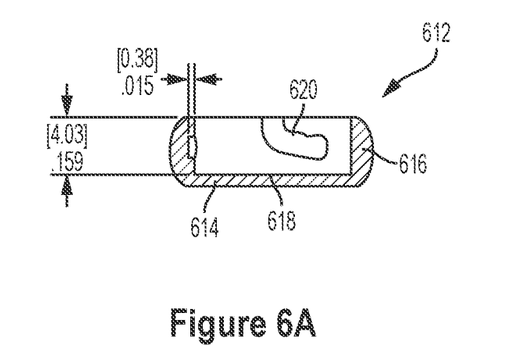
FIGS. 6A-D are four illustrations depicting a base member of a fixation device for use with a housing as disclosed herein, including a cross-sectional view (FIG. 6A), a perspective view (FIG. 6B), a top view (FIG. 6C), and a side view (FIG. 6D), in accordance with various embodiments.
Figure 6B:
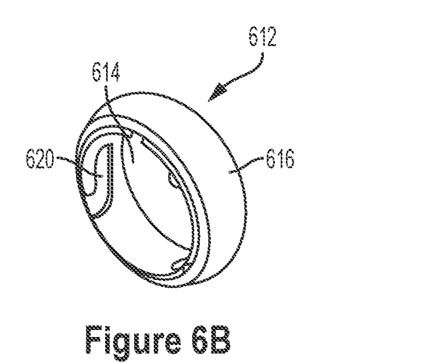
Figure 6C:
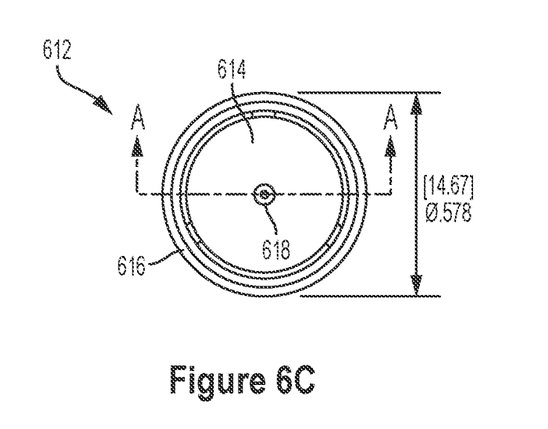
Figure 6D:
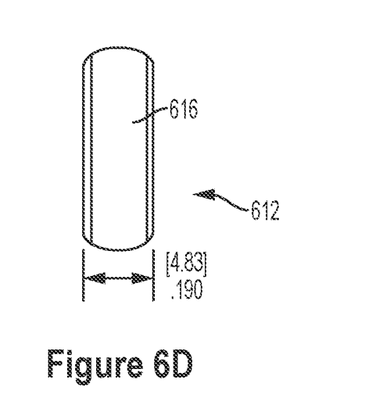
Figure 7A:
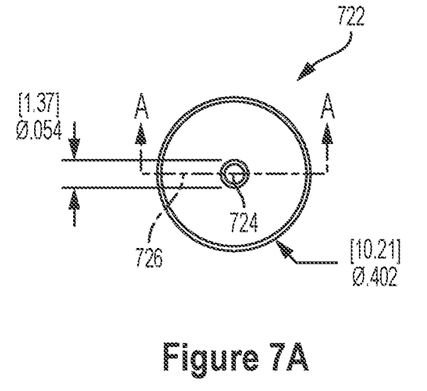
FIGS. 7A-D are four illustrations depicting a pressure plate of a fixation device, including a top view (FIG. 7A), a cross-sectional view (FIG. 7B), a side view (FIG. 7C), and a perspective view (FIG. 7D), in accordance with various embodiments.
Figure 7B:
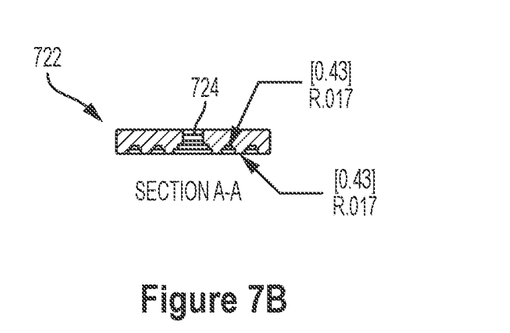
Figure 7C:
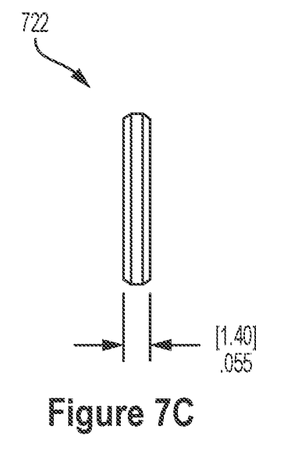
Figure 7D:
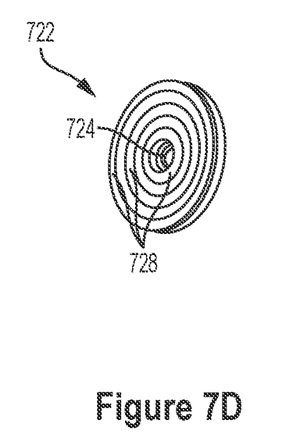

In some embodiments, such as those illustrated in FIGS. 2-4, the housing 100 may be constructed of plastic. FIG. 5 is a 3-D rendering of another example of a feeding tube housing 500 that includes a silicone pad 510, In particular embodiments, such as the embodiment illustrated in FIG. 5, the feeding tube housing 500 may include a silicone pad 510 coupled to a ventral (body-facing) side of the feeding tube housing 500. In particular embodiments, the silicone pad 510 may include an antibacterial composition, such as a silver compound incorporated into the silicone matrix to provide antimicrobial properties.

In various embodiments, the intestine may be secured to the interior of the abdominal wall using a plurality of fasteners, such as T-fasteners, that include a graphene monofilament. As used herein, the term "graphene" refers to an allotrope of carbon in the form of a two-dimensional, atomic-scale, hexagonal lattice in which one atom forms each vertex. In various embodiments, replacing the nylon suture of the conventional T-fastener with graphene fiber suture affords greater tensile strength and flexibility to decrease the amount of shear stress over the skin and decrease the risk of failure and/or complications, especially in obese patients. In some embodiments, each graphene fastener may be permanently affixed to each corresponding fastener receiving hole 106, 506 in the housing 100, 500. In other embodiments, each graphene fastener may be adjustably coupled to each corresponding fastener receiving hole in the housing using a fixation device as disclosed herein.

As disclosed herein, in various embodiments, the disclosed fasteners may be deployed into the bowel lumen, and the suture ends may be adjustably secured in fastener receiving holes, such as by using a fixation device that allows for adjustment of the suture length, and thus may be adjusted to better distribute pressure across abdominal wall and skin. Thus, in various embodiments, the tightness of the fastener may be easily adjusted by adjusting each fixation device, for example to accommodate swelling or increase comfort, or to prevent leaking. In various embodiments, the fixation device may include a base member that fits securely in the fastener receiving hole of a housing member as described above, a pressure plate to receive and secure the fastener, and a locking component to apply pressure to the pressure plate and lock the fastener in place. Each of these components of the fixation device is described in greater detail below.

FIGS. 6A-D are four illustrations depicting a base member 612 of a fixation device for use with a housing as disclosed herein, including a cross-sectional view (FIG. 6A), a perspective view (FIG. 6B), a top view (FIG. 6C), and a side view (FIG. 6D), in accordance with various embodiments. In various embodiments, the base member 612 may be generally cup-shaped, with a disc-shaped bottom portion 614 and a sidewall 616 extending therefrom. In various embodiments, the bottom portion 614 may include a generally central aperture 618 for receiving the suture end of a fastener, and a plurality of angled slots 620 on the interior face of the sidewall 616. In use, the ends of corresponding plurality of protruding tabs on the locking component may be journaled in each of the plurality of opposing angled slots 620, and the angled slots 620 may define a range of movement of the corresponding plurality of protruding tabs as they slide within each slot 620 when the locking component is rotated about the central axis of the base member 612. In some embodiments, slots 620 may include one or more bends, curves, or notches, for example to retain the locking component in the locked position.

FIGS. 7A-D are four illustrations depicting a pressure plate 722 of a fixation device, including a top view (FIG. 7A), a cross-sectional view (FIG. 7B), a side view (FIG. 7C), and a perspective view (FIG. 7D), in accordance with various embodiments. In various embodiments, pressure plate 722 may include a central aperture 724 for receiving the suture end of a fastener from the base member below, and a lateral slot 726 extending from the central aperture 724 to the edge of the pressure plate 722 for receiving and securing the suture end of the fastener in a desired position when pressure is applied from the locking component above. Additionally, in some embodiments, the bottom side of pressure plate 722 may include one or more concentric ridges 728 for compressibility. In various embodiments, the fixation device may be designed to be used with or without the pressure plate 722.

Figure 8A:
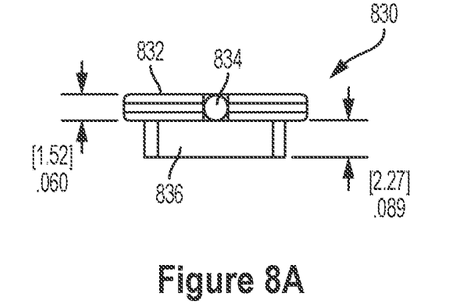
FIGS. 8A-C are three illustrations depicting a locking component of a fixation device, including a side view (FIG. 8A), a top view (FIG. 8B), and a perspective view (FIG. 8C), in accordance with various embodiments.
Figure 8B:
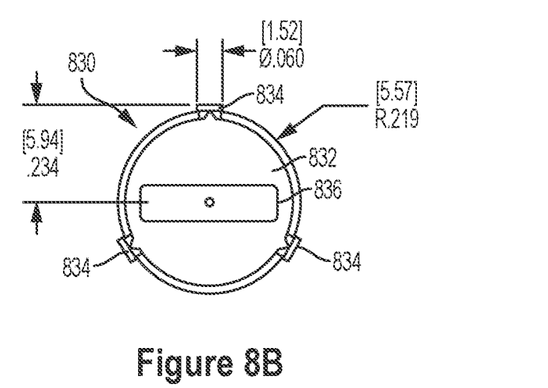
Figure 8C:
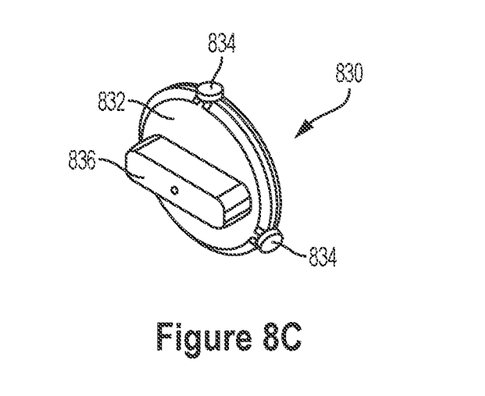

FIGS. 8A-C are three illustrations depicting a locking component of a fixation device, including a side view (FIG. 8A), a top view (FIG. 8B), and a perspective view (FIG. 8C), in accordance with various embodiments. In various embodiments, locking component 830 may include a disc-shaped body 832 with a plurality of protruding tabs 834 that correspond to and are sized to slide within the plurality of angled slots in the base member. In use, the end of each protruding tab 834 may be journaled in a corresponding angled slot in the base member, and the plurality of angled slots may define a range of movement of the protruding tabs as they slide within each slot when the locking component 830 is rotated about the central axis. In various embodiments, a handle 836 may be provided on the upper surface of the disc-shaped body 832 for rotating the locking component within the base member, thus locking the suture end of the fastener within the slot of the pressure plate.

Figure 9:
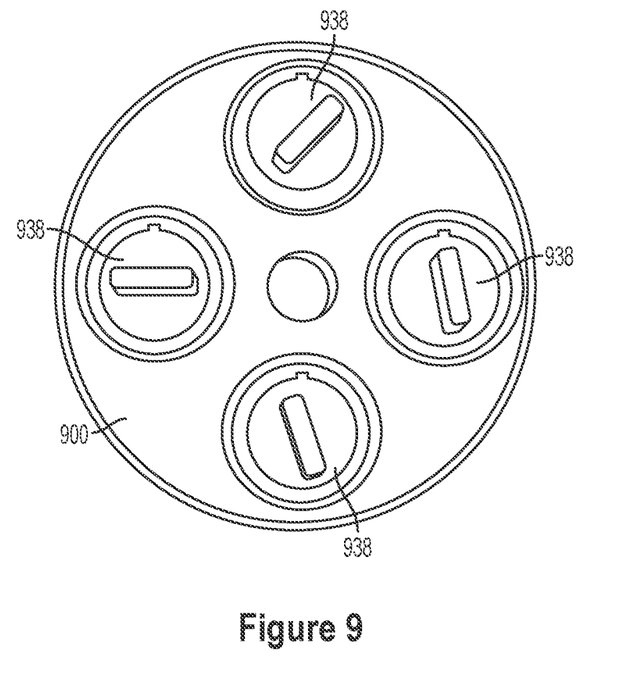
FIG. 9 is a digital image of a third example of a feeding tube housing and four exemplary fixation devices installed therein, in accordance with various embodiments.
Figure 10:
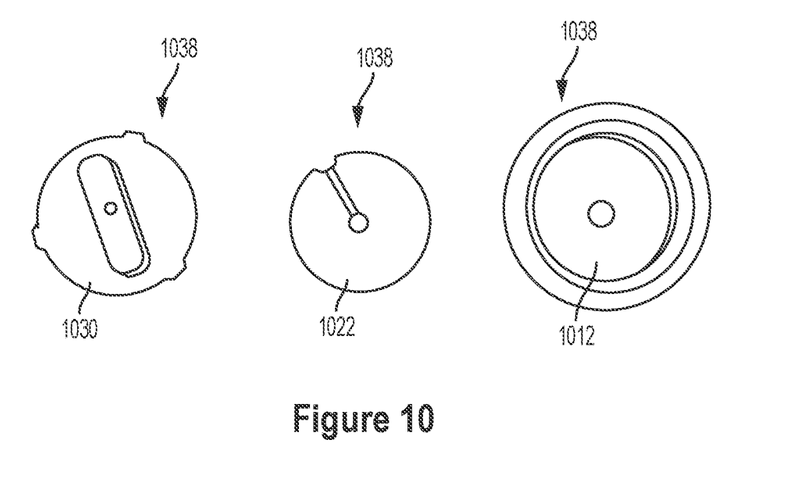
FIG. 10 is a digital image of an example of a fixation device, including a locking component, a pressure plate, and a base member, in accordance with various embodiments.
Figure 11:
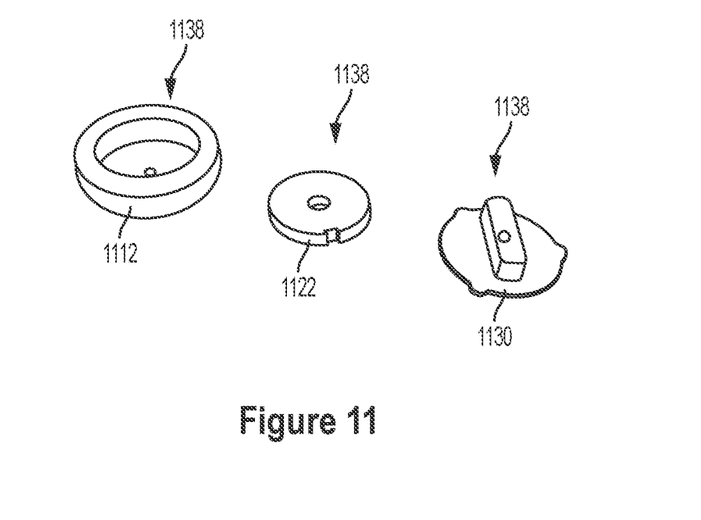
FIG. 11 is a digital image of another example of a fixation device, including a base member, a pressure plate, and a locking component, in accordance with various embodiments.

FIG. 9 is a digital image of a third example of a feeding tube housing 900 and four exemplary fixation devices 938 installed therein; FIG. 10 is a digital image of an example of a fixation device 1038, including a locking component 1030, a pressure plate 1022, and a base member 1012, and FIG. 11 is a digital image of another example of a fixation device 1138, including a base member 1112, a pressure plate 1122, and a locking component 1130, all in accordance with various embodiments.

Figure 12:
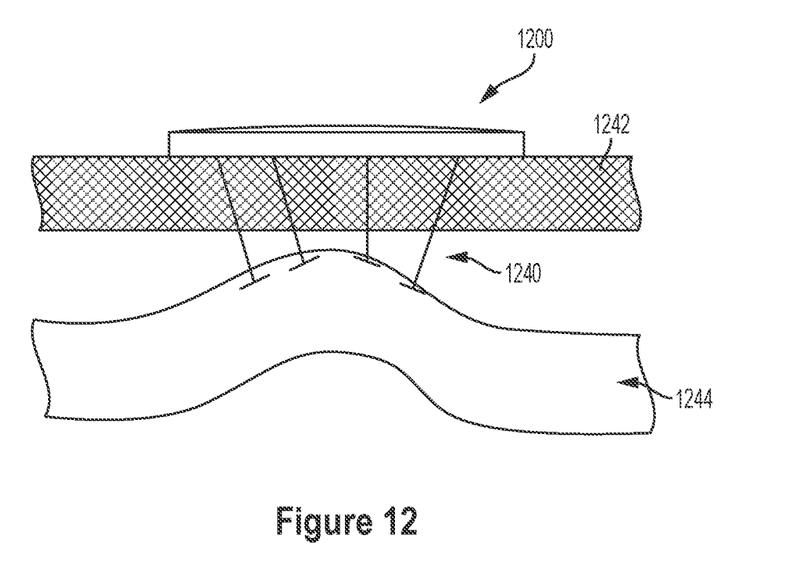
FIG. 12 is an illustration of an example of a feeding tube housing in use, with a plurality of T-fasteners passing through the abdominal wall to secure the bowel to the abdominal wall and allow access to the intestines, in accordance with various embodiments.

FIG. 12 is an illustration of an example of a feeding tube housing in use, with a plurality of T-fasteners passing through the abdominal wall to secure the bowel to the abdominal wall and allow access to the intestines, in accordance with various embodiments. In the illustrated embodiment, each fastener 1240 is anchored in the intestine 1244, and passes through the abdominal wall 1242, where it is externalized and secured by the feeding tube housing 1200. One of skill in the art will appreciate that each fastener 1240 may be secured to the feeding tube housing 1200 in any of a number of ways, including the fixation devices described herein.

EXAMPLES

The following examples are for illustration only. In light of this disclosure, those of skill in the art will recognize that variations of these examples and other examples of the disclosed invention be possible without undue experimentation.

Mechanical laboratory testing may be used to demonstrate material robustness. This testing may include measurement of the tensile characteristics of the graphene T-fasteners, both separately and when combined with the support complex. Lateral and perpendicular shear and tear forces applied by the graphene threads on the foundation also are evaluated, as is the amount of pressure exerted over the silicon padding and distribution of the forces under the padding.

Animal testing is performed to assess the safety and effects of exposure of the skin to the product. Such testing may be done in smaller animals such as rabbits, without the need for jejunostomy. In other tests, the device is placed using laparoscopic surgery in a swine model. Product safety and stability is then evaluated for at least 3 weeks after placement.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An enteric feeding tube housing device comprising:
   a disc comprising a first hole for accommodating a feeding tube;
   a plurality of fastener receiving holes disposed about the first hole;

a base member comprising a bottom portion sized and shaped to fit within one of the plurality of fastener receiving holes and comprising an aperture for receiving a fastener, and a sidewall extending from the bottom portion and comprising a plurality of angled slots disposed on an inward-facing surface of the sidewall; and a locking component comprising a disc-shaped body comprising a plurality of protruding tabs sized to slide within the plurality of angled slots in the base member.

2. The enteric feeding tube housing device of claim 1, wherein the plurality of fastener receiving holes comprises four fastener receiving holes.

3. The enteric feeding tube housing device of claim 1, wherein the disc comprises plastic.

4. The enteric feeding tube housing device of claim 1, further comprising a silicone pad coupled to a body-facing side of the disc.

5. The enteric feeding tube housing device of claim 4, wherein the silicone pad comprises an antibacterial composition.

6. The enteric feeding tube housing device of claim 1, further comprising a perforation disposed about the first hole, wherein the perforation divides the disc into a first section comprising the first hole and a second section comprising the plurality of fastener receiving holes.

7. The enteric feeding tube housing device of claim 6, wherein the perforation is substantially circular.

8. The enteric feeding tube housing device of claim 1, wherein an end of each protruding tab of the plurality of protruding tabs is configured to be journaled in a corresponding angled slot of the plurality of angled slots in the base member, and wherein the plurality of angled slots define a range of movement of the plurality of protruding tabs as each protruding tab of the plurality of protruding tabs slides within the corresponding angled slot of the plurality of angled slots when the locking component is rotated about a central axis.

9. The enteric feeding tube housing device of claim 1, wherein the locking component further comprises a handle for rotating the locking component within the base member.

10. The enteric feeding tube housing device of claim 1, wherein rotation of the locking component reversibly locks a fastener into a desired position.

11. A method of securing a feeding tube, comprising:
securing a portion of an intestine adjacent an abdominal wall with a plurality of fasteners;
externalizing a portion of each of the plurality of fasteners by passing it through the abdominal wall; and
coupling each of the plurality of fasteners to an enteric feeding tube housing device in accordance with claim 1.

12. The method of claim 11, further comprising advancing a feeding tube through the first hole, through the abdominal wall, and into the portion of the intestine.

13. The method of claim 11, wherein the plurality of fasteners comprises T-fasteners.

14. The method of claim 11, further comprising reversibly locking each of the fasteners of the plurality of fasteners to the enteric feeding tube housing using a fixation device.

* * * * *